United States Patent [19]

Zültzke et al.

[11] Patent Number: 4,828,391
[45] Date of Patent: May 9, 1989

[54] TEST-GLASS CHANGER

[75] Inventors: Walter Zültzke, Maintal; Walter Lehnert, Gelnhausen, both of Fed. Rep. of Germany

[73] Assignee: Leybold-Heraeus GmbH, Cologne, Fed. Rep. of Germany

[21] Appl. No.: 881,645

[22] Filed: Jul. 3, 1986

[30] Foreign Application Priority Data

Feb. 14, 1986 [DE] Fed. Rep. of Germany ....... 3604624

[51] Int. Cl.$^4$ ...................... G01N 21/01; G01N 21/13
[52] U.S. Cl. .................................................... 356/382
[58] Field of Search .................. 356/381, 382; 427/10, 427/166, 167

[56] References Cited

U.S. PATENT DOCUMENTS

| | | | |
|---|---|---|---|
| 2,771,055 | 11/1956 | Kelly et al. | 427/10 |
| 3,698,946 | 10/1972 | Kaspaul et al. | 427/10 |
| 4,201,479 | 5/1980 | Lardon | 356/445 |
| 4,582,431 | 4/1986 | Cole | 356/382 |

Primary Examiner—Richard A. Rosenberger
Attorney, Agent, or Firm—Felfe & Lynch

[57] ABSTRACT

Test-glass changer for measuring layer properties optically in vacuum coating installations. A holding device (10) that accommodates several test glasses (12) is rotatably supported on a substrate holder (4), which serves to transport substrates (5) through a stream (22) of coating material. A control mechanism (16) serves to introduce in each case one test glass (12) into a path of rays (A-A) of a measuring device (7,8) and into the stream (22) of coating material. The control mechanism (16) is an incremental motor, by means of which in each case one test glass (12) can be changed over into a position, stationary relative to the substrate holder (4), in which position it can be passed alternately with the substrates (5) through the path of rays (A-A) of the measuring device (8,8) and through the stream (22) of coating material.

5 Claims, 2 Drawing Sheets

TEST-GLASS CHANGER

The invention relates to a test glass changer for measuring layer properties optically in vacuum coating installations, which have a movable substrate holder for guiding at least one substrate on a path through at least one stream of a coating material, with a holding device, which accommodates several test glasses, is supported at these substrate holder and is movable with said substrate holder and movable in itself relative to the substrate holder, and with a control mechanism for introducing in each case one test glass into a path of rays of a measuring device and into at least the one stream of the coating material.

Through the German Offenlegungsschrift No. 2,932,483, a test glass changer of the initially described type is known, for which a constant correlation between the revolutions per minute of the test glass holding device and the revolutions per minute of the substrate holder is fixed by a specified gear ratio. A measurement can therefore be carried out only with the substrate holder stopped in a specified coating position, that is, at a time when the substrate to be coasted and the test glass selected are simultaneously exposed to the flow of a coating material, in that they lie, for example, in the sphere of influence of an atomizing cathode. During this stoppage, the conditions must, of course, continue to be fulfilled that the test glass in question, an opening in the substrate holder, at least one opening in the vacuum chamber and the path of the rays of the measuring device are aligned, that is, that their midpoints lie on a common optical axis. The ratio of the thickness of the layer on the test glass on the one hand to the thickness of the layer on the simultaneously coated substrate on the other is of course subject to the distribution of layer thicknesses specified by the coating source, so that the measured values do not necessarily have to agree with the actual layer thickness. In the known solution, the test glass selected is disposed in the center of a group of substrates coated simultaneously, that is, at a place at which the rate of deposition of the coating material usually is particularly high. The known solution moreover requires the substrates to be combined groupwise on individual substrate plates which, in turn, are supported in the carousel-like substrate holder. This construction furthermore requires each group of substrates or each coating station (as a rule, several coating stations are provided for alternating sequence of layers) is provided with its own test glass changer and its own measuring device, so that the expenditure for construction is increased appreciably. A construction as expensive as this, the discontinuous mode of operation (without relative movement between the substrates and the coating source) imposed by the rigid coupling of the test glass changer to the substrate holder, as well as the deviations between the measured results an the properties of the substrates are, however, intolerable for numerous cases of application.

It is therefore an object of the invention to improve a test glass changer of the initially described type so that the expense of constructing the whole of the vacuum coating installation is reduced, a continuous mode of operation becomes possible and the deviations between the measured results and the properties of the substrate are reduced to a minimum.

This objective with respect to the initially described test glass changer is accomplished inventively owing to the fact that the control mechanism is an incremental motor, by means of the which in each case one test glass can be changed over a path, which is short relative to the complete path length of the substrate holder, into a position, which is stationary relative to the substrate holder and in which it can be passed with the substrate for a specified number of rotations of the substrate holder alternately and consecutively through the path of rays of the measuring device and through the stream of coating material.

The movement of the substrate holder may be a linear, oscillating motion or a rotary motion. In the latter case, the "path length" then is the periphery at an angle of rotation of 360 degrees.

As a result of the inventive solution, only a single test glass changer is required for each coating installation,- the selected test glass in each case being moved continuously through the individual coating stations in the same manner as the substrate. As a result of this, first of all construction costs are reduced appreciably, since only a single measuring device is required. If the substrate is disposed on a circular path, on which the selected test glass is also located, the test glass as well as all the substrates have th same layers an therefore also the same measurement results or properties. In this connection, it is of course assumed that the flow of material from the source does not change during one or several cycles of the substrate holder which, however, is easily achievable in practice. The continuous mode of operation leads to a higher productivity of the coating installation and it is not necessary to hold the selected test glass in the path of the rays of the optical measuring device for the duration of the coating process. Rather, the measurement can be carried out as the test glass passes through the ray of beams, a synchronizing device ensuring that the signals are not processed while the path of the rays interrupted (with the exception of when the test glass is traversing the ray of beams). The measures and means for this area known to those skilled in the art, so that it is not necessary to consider these here in greater detail.

The object of the invention can be used to particular advantage in those coating processes, in which alternating layers of material of high and of low refractive index are applied. Such sequences of layers are also referred to as "interference systems".

From the aforementioned German Offenlegungsschrift No. 2,932,483 and the German Offenlegungsschrift No. 2,750,421 of the same applicant, it is furthermore already known that it is particularly advantageous with such systems of layers to apply the material of high refractive index on one test glass and the materials of low refractive index on a different test glass in order thus to be able to measure the sinoidally fluctuating transmission and reflection ratios over a large number of layers without attenuation. In such a case with the inventive object, the substrate and one of the test glasses are simply allowed to pass through the flow of coating material (for example, with a high refractive index), it also being possible to build up such a layer from indentical individual layers through a large number of passes. During further cycles of the substrate holder, the change-over of the test glass changer is simply omitted in such a case by procedures, which will be explained more closely in the detailed description. Only when the coating material is changed (for example, to one with a low refractive index) is there a change-over to a different test glass, on which now one or more layers of the material in question are built up. Subsequently, if a layer of the first material is applied once more, it is possible, for example, to change over to the test glass used first if, for example, the test glass changer holds two test glasses in symmetrical arrangement. It is, however, also possible to provide the test glasses in a number, which corresponds to an even-number multiple of the different coating materials, that is, for example four test glasses, so that, when the coating material is changed, the test glasses move forward in each case in a similar manner. In this case also, the materials of high refractive index on the one hand an the materials of low refractive index on the other are always deposited on different test glasses.

The object of the invention has, however, proven its value also and in particular with those layers, which comprise only a single substance. In this case, a magazine for an appropriate number of test glasses is made available by the inventive test glass changer.

In this connection, it is, moreover, particularly advantageous if the holding device for the test glasses is a circular disk, which has several recesses for the test glasses on a concentric circle and if it can be moved forward intermittently by the control mechanism about an axle, fixed relative to the substrate holder, according to the angular distance between the recesses and if it is covered by a protective device, which, in each case, leaves only a single test glass open in its coating and measuring position.

Such a test glass changer can be moved forward most simply and easily controllably by a type of indexing device, which will be explained more closely in the detailed description.

Further advantageous developments of the inventive object arise out of the remaining dependent claims.

An example of the operation of the object of the invention is explained in greater detail in the following by means of FIGS. 1 and 2, which show a device with a rotatable substrate holder.

Figure 1:
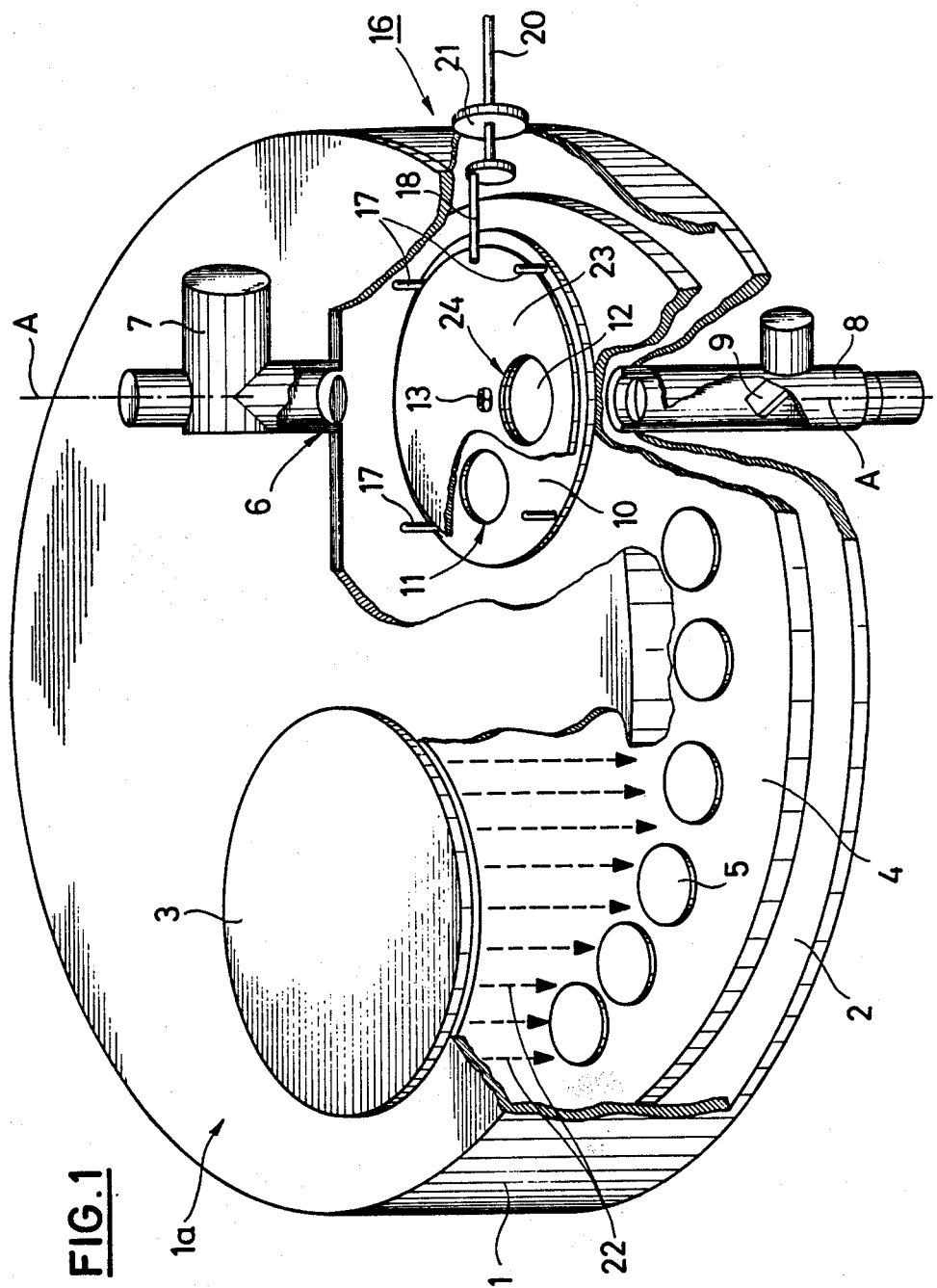
FIG. 1 shows a partially opened up, prespective representation of a complete vacuum coating installation with the inventive test glass changer.

In FIG. 1 a vacuum coating installation is shown, which is constructed as a cathode sputtering installation. The installation has a cylindrical vacuum chamber 1, the lower end of which is formed by a bottom 2. In the cover of the cylinder, a sputtering cathode 3 is disposed, and it is pointed out that such an installation may also be equipped with two or more such sputtering cathodes. In the bottom 2, there is a pivot bearing (not shown here) for a substrate holder 4, which is constructed as a circular disk, which can be cooled. On this substrate holder and within a concentric, circular movement path 4a (FIG. 2), there is a series of substrates 5, with are passes by the rotation of the substrate holder 4 through a stream of coating material, which emanates from the sputtering cathode 3.

In the cover 1a of the vacuum chamber, an opening 6 is disposed, in which a light source 7, which defines the optical axis A—A of a path of rays, is inserted vacuum-tight. At a coaxial opposite place, there is in bottom 2 a further opening, in which a receiver part 8 with a photosensor 9 is inserted vacuum-tight and with the same path of rays. Light source 7 and receiver part 8 together form an optical measuring device, the path of rays or the optical axis A—A of which lies in the path of motion 4a of the substrates 5.

On the upper side of the substrate holder 4, a holding device 10 is rotatably and excentrically supported. Said holding device is constructed as a circular disk and, in equidistant arrangement on a concentric circle, has several recesses 11 for a number or test glasses 12. The holding device 10 can be rotated about an axle 13 which, in turn, is rigidly connected with the substrate holder 4.

Figure 2:
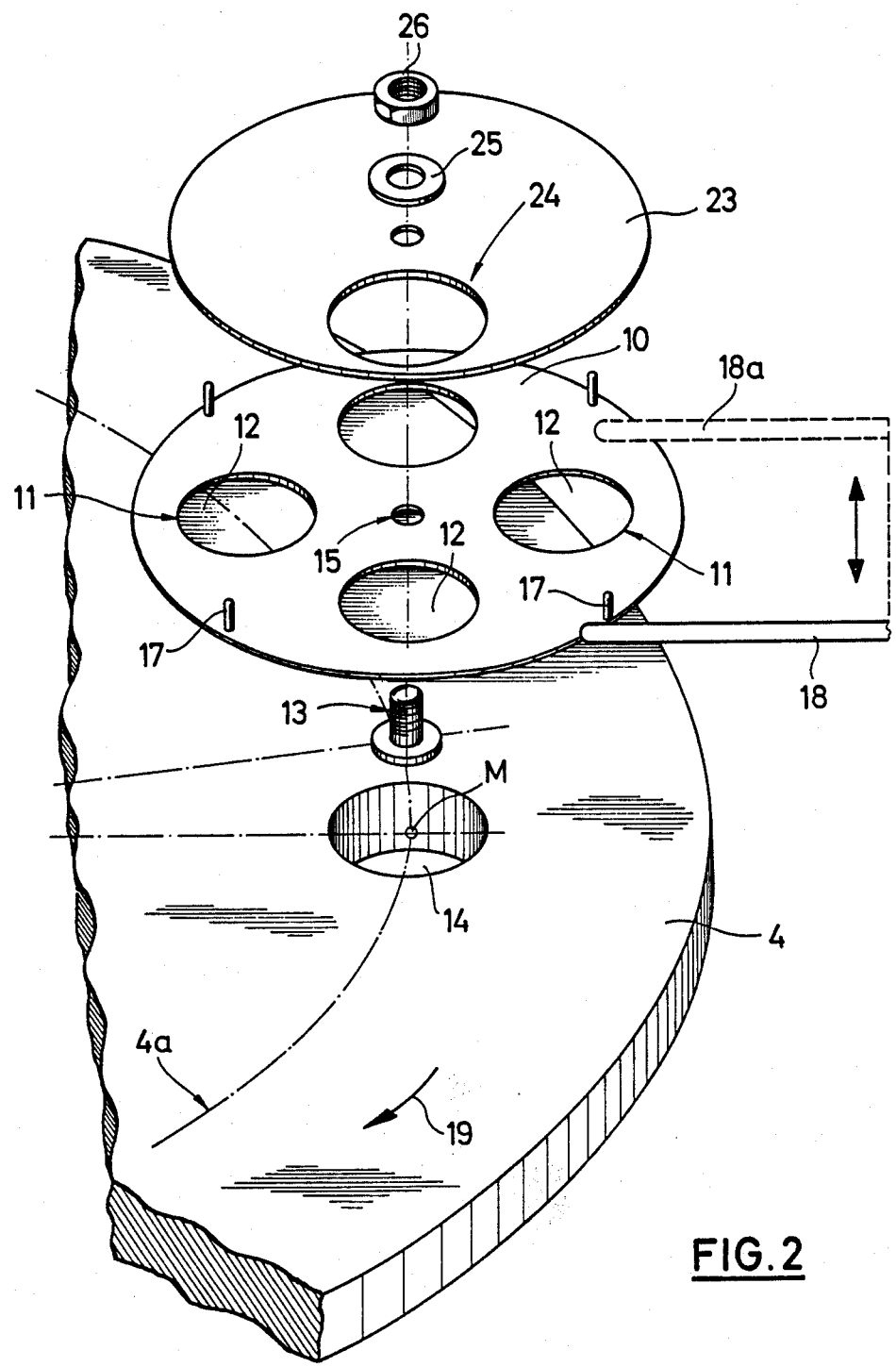
FIG. 2 shows an exploded diagram of the test glass changer of FIG. 1 in conjunction with a partial section of the substrate holder.

As can be seen by including FIG. 2, there is in substrate holder 4 a hole 14, the midpoint M of which lies on the same path of motion 4a as the midpoints of the substrates 5. By means of a central hole 15, the holding device 10 can be slipped onto the axle 13, the arrangement being made so that each of the recesses 11 in the holding device 10 can be brought by rotation into a position congruent with the hole 14. This intermittent advance is accomplished by means of a control mechanism 16, which is in the form of an incremental motor and to which belong a number of pin-shaped projections 17, which work together with a movable switching finger 18. The projections 17 correspond in number to the number of recesses 11 or of test glasses 12 and are disposed on the periphery of the holding device 10 at the same angular interval as the recesses. In one of the its possible positions, the switching finger 18 projects into the circular path of the projection 17, which lies furtherst to the outside about the midpoint of the substrate holder 4. If the right edge of the substrate holer 4, visible in FIG. 2, rotates forwards in the direction of the arrow 19, projection 17, which lies directly in front of the switching fingers 18, comes up against switching finger 18 and is restrained until it slides off again from the switching finger 18 after the holding device 10 has rotate through 90 degrees (360 degrees divided by the number of recesses 11). At the same time, a test glass 12 leaves it position congruent with hole 14 and the next test glass moves into its place. Thus, as the substrate holder 4 rotates slightly, the holding device 10 is moved forward by the angular distance between two immediately adjacent recesses 11. For the remainder of the rotational movement of the substrate holder 4, the holding device 10 is kept in a position of rest relative to the substrate holder.

The switching finger 18 can be raised vertically upwards from the position shown by the solid line into the position 18a shown by the broken line, in which position it no longer projects into the circular path of one of the projections 17. In this case, there is thus no forward motion and, by these means, one has the possibilitly of preventing the forward motion of the test glass changer for a given number of revolutions of the substrate holder. A further possibility of moving the switching finger is shown in FIG. 1, in which the switching finger is mounted excentrically on a shaft 20, which leads through a vacuum-tight rotating guide into the interior of the vacuum chamber 1. The "selected test glass" in each case is that which, for the purpose of a coating and measurement, is in a position congruent with the hole 14.

The vertical arrows in FIG. 1, indicated by broken lines, symbolize the stream 22 of the coating material. The holding device 10 is covered by a protecting device 23, which in each case leaves only a single test glass 12 exposed in its coating and measurement position. The protective device moreover is a circular disk, which cannot rotate relative to the substrate holder 4, lies coaxially on the holding device 10 of the test glasses 12 and has a single opening 24, which can be made to coincide with one of the test glasses 12. The protective device 23 is fixed by a washer 25 and a nut 26 on axle 13 so that it cannot rotate, and moreover in a position of congruence with the hole 14.

As can be seen especially from FIG. 1, the diameter of the protective device is smaller than the diameter of the holding device 10 by such a measure, that the projections 17 can run freely around the protective device 23.

The test glass changer described allow the substrate and the respective test glass elected to be moved consecutively on the same path through the stream 22 of the coating material, so that the conditions existing at the substrates and the test glass are identical. When the control device 16 intervenes, the test glass holding device is moved forward through an angle of rotation, which is small in relation to complete rotation of the substrate holder. For the greater part of the circumferential path of the substrate holder, however, the test glass holding device is at rest relative to the substrate holder.

As the selected test glass passes through the optical axis A—A of the measuring device, the layer properties on the test glass are measured, the short time span available for optically scanning the test glass due to the synchronization circuit described above being completely adequate.

While FIG. 1 shows a measuring device for a so-called transmission measurement, it is of course possible to dispose the light source and the receiver on one and the same side of the test glass changer, so that a so-called reflection measurement is also possible. For reflection measurements from above, the hole in the substrate holder can be omitted, which offers further advantages when a bias voltage is applied to the substrate holder.

We claim:

1. A test glass changer for measuring layer properties optically in vacuum-coating installations comprising:
    a movable substrate holder for guiding at least one substrate on a path through at least one stream of a coating material;
    a holding device which accommodates several test glasses and which is supported at the substrate holder and which is movable with the substrate holder and movable in itself relative to the substrate holder; and
    a control mechanism for introducing a test glass of a plurality of test glasses into a path of rays of a measuring device and into the at least one stream of the coating material, the control mechanism comprising incremental motor means for bringing, during continuous movement of the substrate holder, the test glasses selectively into such a position during movement of the substrate holder that each of the test glasses is coated by one and the same material in the at least one stream of the coating material.

2. A test glass changer as defined in claim 1, wherein the holding device for the test glasses is a circular disk, which has several recesses for the test glasses at an angular distance from each other on a concentric circle and can be moved forward intermittently by the control mechanism about an axle, fixed relative to the substrate holder, according to the angular distance between the recesses and wherein the holding device is covered by a protective device, which leaves only a single test glass open in its coating and measuring position.

3. A test glass changer as defined in claim 2, wherein the protective device is a circular disk, lying coaxially on the holding device for the test glasses and being non-rotatable with respect to the substrate holder, said circular disk having a single opening which can be brought into coincidence with one of the test glasses.

4. A test glass changer as defined in claim 3, wherein the substrate holder has an opening at the place of the opening in the protective device.

5. A test glass changer for measuring layer properties optically in vacuum-coating installations comprising:
    a movable substrate holder for guiding at least one substrate on a path through at least one stream of a coating material;
    a holding device which accommodates several test glasses and which is supported at the substrate holder and which is movable with the substrate holder and movable in itself relative to the substrate holder; and
    a control mechanism for introducing a test glass of a plurality of test glasses into a path of rays of a measuring device and into the at least one stream of the coating material, the control mechanism comprising means for bringing the test glasses selectively into such a position during movement of the substrate holder that each of the test glasses is coated by one and the same material in the at least one stream of the coating material, wherein the holding device for the test glasses is a circular disk, which has several recesses for the test glasses at an angular distance from each other on a concentric circle and can be moved forward intermittently by the control mechanism about an axle, fixed relative to the substrate holder, according to the angular distance between the recesses and wherein the holding device is covered by a protective device which leaves only a single test glass open in its coating and measuring position, and wherein the control mechanism comprises a number of projections having a circular path and corresponding to the recesses, said projections being disposed at the periphery of the holding device at the same angular distance as the recesses, as well as a switching finger, which can be moved into the circular path of the projections and by means of which the holding device can be moved by one angular distance between two recesses.

* * * * *